United States Patent [19]

Failing

[11] 4,299,240
[45] Nov. 10, 1981

[54] METHOD FOR STYLING HAIR

[76] Inventor: Coleda J. Failing, 2109 W. Broadway, Oklahoma City, Okla. 73701

[21] Appl. No.: 52,447

[22] Filed: Jun. 26, 1979

Related U.S. Application Data

[63] Continuation-in-part of Ser. No. 879,275, Feb. 21, 1978, abandoned.

[51] Int. Cl.$^3$ ............................................. A45D 7/00
[52] U.S. Cl. .......................................... 132/7; 424/71
[58] Field of Search .................. 132/7, 9; 424/71, 94, 424/81, DIG. 2

[56] References Cited

U.S. PATENT DOCUMENTS

| | | | |
|---|---|---|---|
| 1,833,538 | 11/1931 | Sandor | 132/7 |
| 2,190,057 | 2/1940 | Doerr | 132/7 |
| 2,265,656 | 12/1941 | Snyder | 132/7 |
| 3,186,911 | 6/1965 | Rieger et al. | 132/7 |

Primary Examiner—G. E. McNeill
Attorney, Agent, or Firm—Dunlap, Codding & McCarthy

[57] ABSTRACT

An improved method for styling hair comprising the steps of applying a stable foam to dampened hair to form a pliable hair and foam mass, shaping the hair and foam mass as desired, drying the shaped mass of hair and foam, and combing the hair to remove the foam residue. After the foam residue is combed out, the hair is retained in the desired style.

5 Claims, No Drawings

METHOD FOR STYLING HAIR

CROSS-REFERENCE TO RELATED APPLICATION

This is a continuation-in-part of co-pending application, Ser. No. 879,275, filed Feb. 21, 1978 now abandoned.

BACKGROUND OF THE INVENTION

1. Field of the Invention

The present invention relates generally to the field of cosmotology, and more particularly, but not by way of limitation, to an improved method of styling hair utilizing stable foam as a hair training aid.

In one aspect, the invention relates to an improved method of styling hair utilizing stable foam as the hair training aid without the use of mechanical hair styling aids.

2. Discussion of Prior Art

A typical session at a hair stylist or beauty shop usually begins with washing, shampooing and thoroughly cleansing a customer's hair. Next, the hair is shaped, formed and set with mechanical hair styling aids such as rollers, curlers, pins or the like. This is followed by drying the damp hair for a relatively lengthy time of about forty-five minutes to an hour. The styling session is generally finished with a final brushing of the dried hair.

The proper setting of hair is time consuming, since each roller, or the like, must be individually attached to a portion of the hair. The best results are achieved when a large number of relatively small rollers are used, as opposed to using only a few large or jumbo rollers, principally because of the ability to form tighter curls with small rollers, but also because of the large space left between adjacent rollers when larger rollers are used. Due to the time consuming nature of attaching a large number of small rollers, hair stylists will frequently use a lesser number of medium size rollers. As a result, the hair cannot be as finely styled as the customer would prefer. However, due to economic considerations, this is a necessary part of the compromise which the customer accepts for the price paid.

It is usually expected that a drying time of forty-five minutes to an hour (and sometimes longer) will be necessary to thoroughly dry damp hair which has been styled and set with styling aids as described above. While this presents an undue demand on the customer's time, it also represents a major factor in the operator's overhead cost. Furthermore, the longer that a person's hair is subjected to the hot air of a dryer, the greater the risk that the hair will incur damage.

After the hair is thoroughly dry, the rollers, or other such styling aids, are removed. Of course, the hair generally remains in the shape impressed thereupon by the styling aids. However, since the rollers are essentially utilized to apply a temporary tension or pressure upon the hair, the hair usually tends to spring back toward its natural un-styled form when the styling aids are removed. The degree to which the hair resumes its normal state is determined by the inherent characteristics of each persons's hair. Therefore, a beauty operator can never predict or determine in advance the precise manner in which a customer's hair should be set in order to provide a desired style. The somewhat unpredictable outcome of a styling session is generally compensated for, at least to some degree, by final brushing of the hair after drying and removing of the rollers. The final brushing gives body to the hair, since the hair tends to become compacted when the hair is dried following being dampened. However, too much brushing, or a brush in the hands of a less than skilled operator, can be detrimental to the completed hairdo.

All things considered, it should be clear that conventional hair styling methods and techniques, while representing the latest in modern styling techniques, have undesirable characteristics and remain an uncomfortable necessity. Furthermore, because of economic considerations, hair stylists cannot provide their customers with quality hair styling at what most persons consider to be a reasonable price.

SUMMARY OF THE INVENTION

The present invention provides an improved method of styling hair utilizing a stable foam, defined more fully hereinbelow, in lieu of mechanical hair training aids that were discussed above. That is, a stable foam forms with the hair a pliable mass that can by styled and retained in a selected setting without the use of curlers, rollers, bobbypins and the like. The method comprises the steps of applying a stable foam to a person's damp hair to form a pliable mass of hair and foam; shaping the pliable mass to a predetermined sculptured shape that is retained as a setting by the foam; drying the shaped hair and foam mass so as to set the hair into a semi-rigid sculptured shape, the foam dissipating upon the application of heat; and finally, brushing the hair to shape the hair, which simultaneously removes any foam residue on the hair.

The result is a hair styling technique that provides the operator greater versatility in creating hair styles, provides greater predictability during the hair styling process as to the final outcome of the styling, permits tighter hair manipulations that are unrestricted by mechanical aids, and provides for the creating of improved quality hairdos that require less time and effort.

Accordingly, it is an object of the present invention to provide an improved hair styling method that gives a stylist greater versatility in creating new hair styles while providing greater predictability as to the outcome of the styling.

Another object of the present invention while achieving the above stated object is to provide an improved method for setting hair that requires a minimum of time and effort.

Another object of the present invention while achieving the above stated objects is to provide an improved hair setting method that prevents the deleterious effects on the hair that are inherent in prior art hair styling techniques.

Another object of the present invention while achieving the above stated objects is to provide an improved hair setting method that provides a hair stylist with the insight and ability to control the styling of hair by knowing, during the hair styling process, how a finished hairdo will appear. Another object of the present invention while achieving the above stated objects is to provide an improved hair setting method that permits tighter hair manipulations that are unrestricted by mechanical aids.

Other objects, advantages and features of the present invention will become apparent to the persons skilled in the art of hair styling from reading the following description of the present invention in conjunction with the appended claims.

DESCRIPTION OF THE PREFERRED EMBODIMENT

The present invention provides a method employing a stable foam for setting, shaping and styling hair. The foam is utilized in lieu of conventional mechanical styling aids to retain damp hair in a predetermined shape or configuration during and after drying of the hair. Thus, a hair stylist practicing the present invention can give a customer a hairdo that more fully meets the customer's expectations without concern as to losing the "set" of the hair after removing mechanical styling aids. As a clarification, mechanical styling or training aids as used herein are defined as conventional hair styling utensils, such as rollers, curlers, pins and the like.

For a fuller appreciation and full understanding of the present invention, a discussion will now be provided of the foam utilized in practicing the invention. In addition to the prior art steps discussed above in the conventional styling of hair, a wave lotion is sometimes used to set hair. After the hair has been rolled onto the mechanical styling aids, the hair is wetted with any of several wave lotions that are commercially available, the function of such wave lotions being to add "memory" to the hair, the term memory meaning that each curl is caused to retain some curling shape following drying.

When wave lotions are used, a number of means of application have been available, as such wave lotions are available in the form of liquids, gells, and foams. However, the prior art foams were not used as in the present invention, as they were formulated to be merely a vehicle to carry the wave lotion, and the foam was formulated to rapidly dissipate upon contact with the hair, or upon rubbing. A good discussion of hair fixatives, such as wave lotions, can be found in U.S. Pat. No. 3,972,336 issued to Nowak, Jr. et al., and a discussion of foams appears in U.S. Pat. No. 3,131,152 issued to Klausner.

Numerous self-propelling liquid formulations are available commercially for creating foams. Such formulations, when dispensed, produce either stable foams, semi-stable foams or atomized sprays. Formulations producing stable foams are used, for example, as shaving or shampoo lathers. Formulations producing atomized sprays find utility as after-shave lotions, cold-wave lotions, nail polish removers, etc. The Klausner patent teaches a foam dispersent that produces a foam of limited stability that does not become completely liquified when exposed to the atmosphere, but which, when disturbed as by rubbing, reverts quickly to a liquid.

The term stable foam as used herein is to be understood to mean a foam which does not deteriorate or dissipate at ambient temperatures for a period of time of at least about 5 minutes, preferably for a period of time of at least about 20 minutes.

Thus, a stable foam is one that remains as a foam for a substantially long period of time when exposed to the atmosphere and does not quickly revert or breakdown to a liquid or solid. Further, such stable foam will remain foamy and pliable for a relatively long period of time even under the influence of being worked or manipulated by the hands of the user. Yet, when exposed to the higher temperatures of a hair dryer, the foam will quickly dissipate leaving little or substantially no residue.

For use in the practice of the present invention, it has been found that several foaming preparations are commercially available that will work. Through experimentation with several such foaming preparations, it has been determined that the best that is presently known is a product manufactured under the name of "Woolite Spray Foam Rug Cleaner", a product that safely cleans a variety of materials, both synthetic and natural. "Woolite" is a trademark of Boyle-Midway, Inc. of New York City.

While there are other preparations that will perform adequately, and while the complete mechanism of operation is not fully understood, the "Woolite" product just mentioned operates effectively in the practice of the present invention. Since this product is a cleaning agent, the ingredients are not believed to be as important as is the quality of foam generated by such a product. That is, the foam needs to stand up well under the process of configuring the hair, and it must dissipate with a minimum of residual material being formed upon drying, with the residual material being easily removed in the final brushing of the hair. Also, the foam preparation must not adversely react to the skin of the person.

In addition to the above, stable foam compositions for use in the method of the present invention can be formulated. Such stable foam compositions are aqueous compositions which contain water as a major constituent. In addition to the water, the foam composition consists of a minor effective amount of a surfactant capable of producing a foam, and a minor effective amount of a substantially water dispersible polymeric material represented by the general structure:

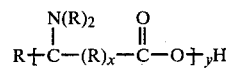

wherein each R is independently selected from H, an alkyl group containing from 1 to about 20 carbon atoms, or an amino-substituted alkyl group containing from 1 to about 20 carbon atoms; y is an integer of 0 or 1; and x is an integer of from 2 to about 200. For use as a hair sculpturing foam composition in accordance with the present invention, the composition must be capable of producing a stable foam which readily dissipates upon the application of heat without leaving any substantial amount of visible residue on the hair. Further, the foam properties of the composition must be such that the foam remains stable and does not substantially deteriorate for a period of time effective to allow the hair stylist to style the pliable mass resulting from the application of the composition to the hair. Any suitable surfactant which is capable of producing, in the presence of the above defined substantially water dispersible polymeric material, a stable foam, can be employed in the hair sculpturing foam composition of the present invention, provided such surfactant does not harm the individual or the hair. Example of surfactants fulfilling the above requirements are anionic surfactants and nonionic surfactants.

Typical anionic surfactants which can be employed as the surfactant constituent in the hair sculpturing foam composition of the present invention are alcohol ether sulfates, alkyl sulfates, and linear alkylbenzene sulfonates. The alcohol ether sulfates can be the reaction product of alcohol ethoxylates which have been reacted with a sulfating agent, such as sulfuric troxide or chlorosulfonic acid, and thereafter neutralized with a base, such as sodium hydroxide or ammonium hydroxide, to produce the class of anionic surfactants generally known as alcohol ether sulfates. Typical alcohol ethoxylates which can be employed to produce the alcohol ether sulfates are the alcohol ethoxylates containing from about 12 to about 14 carbon atoms, and mixtures thereof, which have been ethoxylated to about 40 percent with ethylene oxide.

The alkyl sulfates can be produced by reacting an alcohol, such as an alcohol containing from about 10 to about 20 carbon atoms, with a sulfating agent, such as sulfur trioxide or chlorosulfonic acid, and thereafter neutralizing the sulfated product with a base, such as alkali metal hydroxide or ammonium hydroxide, to produce the alkali metal or ammonium salt of an alkyl sulfate, a class of anionic surfactants commonly referred to alkyl sulfates. Typical nonionic surfactants which can be employed as the surfactant of the hair sculpturing foam composition of the present invention are the nonionic alcohol ethoxylates. Such nonionic alcohol ethoxylates can be produced by reacting an alcohol containing at least about 10 carbon atoms with ethylene oxide to produce the alcohol ethoxylates. Desirably, the alcohol will contain from about 10 to 12 carbon atoms, and blends thereof, and the alcohol will be ethoxylated to about 60 percent with ethylene oxide.

Linear alkylbenzene sulfonates can be produced by alkylizing a linear chloroparaffin or olefin with benzene and thereafter sulfonating and neutralizing the resulting alkylate product. Generally the alkyl moiety of the linear alkylbenzene sulfonates will contain from about 10 to about 18 carbon atoms and the neutralizer agent will be sodium hydroxide.

While any of the above surfactants can be employed, the anionic surfactants, such as the alkali metal salts of an alkyl sulfate, the ammonium salts of an alkyl sulfate, or mixtures thereof, are preferred. The alkyl moiety of the alkyl sulfate can vary widely but will generally range from about 10 to about 16 carbon atoms, including mixtures thereof. The cation moiety of the surfactant will generally be sodium or ammonium. Typical examples of such sodium and ammonium alkyl sulfates are sodium lauryl sulfate, ammonium lauryl sulfate, sodium mysistyl sulfate, ammonium mysistyl sulfate, sodium cetyl sulfate, and ammonium cetyl sulfate.

A second ingredient of the air sculpturing foam composition of the present invention is the substantially water dispersible polymeric material represented by the general structure:

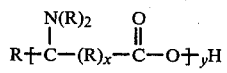

wherein each R is independently selected from H, an alkyl group containing from 1 to about 20 carbon atoms, or an amino-substituted alkyl group containing from 1 to about 20 carbon atoms; y is an integer of 0 or 1, and x is an integer of from 2 to about 200. Any suitable water dispersible polymeric material meeting the above definition can be employed, provided such composition is not toxic to the person or harmful to the hair of the person. A typical dispersible polymeric material satisfying the above definition is gelatin, a proteineous polymer formed by the polymerization of a mixture of amino acids.

The amount of surfactant employed in the hair sculpturing foam composition can vary widely and will be dependent, at least in part, on the particular surfactant employed. However, the surfactant should be employed in a minor effective amount to impart the desired foam properties to the composition. Generally such can be accomplished if the surfactant is employed in an amount of at least about 0.01 weight percent, preferably from about 0.1 to about 2.5 weight percent, based on the total weight of the composition.

The amount of the water dispersible polymeric material can also vary and will be dependent upon the properties of the water dispersible polymeric material and the surfactant employed. However, the water dispersible polymeric material should be employed in a minor effective amount to assist in stabilizing the foam. Thus, the amount of the water dispersible polymeric material employed in the hair sculpturing foam composition of the present invention can generally range from 0.6 to about 1.9 weight percent, based on the total weight of the foam composition. Generally, however, the polymeric material will be employed in an amount of from about 1.0 to about 1.5 weight percent, based on the total weight of the composition.

In addition to the water, the surfactant, and the water dispersible polymeric material, it may be desirable to incorporate other additives into the hair sculpturing foam composition to impart certain characteristics to the hair, such as softness, sheen, body, fragrance, and the like. For example, it is often desirable that the foam composition have incorporated therein a minor effective amount of a hair softening agent to impart softness to the hair. Such can generally be accomplished by incorporating into the composition an effective minor amount, of a softening agent having a basic pH, such as ammonia, ammonia containing compounds or amino compounds. Typical of such ammonium containing compounds are ammonium hydroxide, whereas, typical amino compounds are pyridine, and the hydrolyzed product of gelatin. Hydrolysis procedures are well known in the art. A typical procedure for hydrolyzing gelatin is as follows: an aqueous admixture of gelatin is acidified, such as with HCl, to a pH of about 2. The resulting admixture is thereafter heated to a predetermined temperature for a period of time effective to allow the hydrolysis of gelatin to go to substantial completion. Desirably, the admixture is stirred, at least intermittantly, during the reaction period. Thereafter, the reaction mixture containing the hydrolyzed gelatin is neutralized to a pH of about 7.5.

The hydrolyzed gelatin, when analyzed using infrared spectroscopy, contains amino acids and other constitutents which form gelatin as follows: alanine, 8.7%; arginine, 9/9%; aspartic acid, 3.4% cystine, 0.1% glutamic acid, 5/8%; glycine, 25.5%, histidine, 0.9%; hydroxyproline, 14.4%; leucine, 7.1%; lysine, 5.9%; phenylalamine, 1.4%; proline, 9.5% and fibrin, 8%.

When employing ammonia containing compounds as a softening agent, it may be desirable to incorporate into the hair sculpturing foam composition perfumes and the like. Further, other ingredients, such as colorants and the like may be incorporated into the foam composition in minor amounts. However, when employing other perfumes, colorants, or the like, care must be exercised to insure that the ingredients are inert and do not react with the other components of the foam composition.

In order to provide additional body to the hair, both during this initial sculpturing process and after the hair has been dried and the foam has been dissipated, it may be desirable to incorporate into the foam composition a minor effective amount of a water-dispersible polyvinyl alcohol. The molecular weight of the polyvinyl alcohol can vary widely but will generally be at least about 25,000, and desirably from about 25,000 to about 150,000. In addition, the polyvinyl alcohol may be hydrolized prior to incorporation into the foam composition.

The amount of the polyvinyl alcohol or hydrolized constituent thereof incorporated into the foam composition can vary widely. However, it is generally desirable, when incorporating polyvinyl alcohol or the hydrolyzed derivative of polyvinyl alcohol into the foam composition, that the polyvinyl alcohol or hydrolized derivative thereof be incorporated in an amount of from about 0.01 to about 0.5 weight percent.

With the above discussion of stable foam in mind, the present invention will now be more fully described. Basically, the method of the present invention comprises the steps of applying a stable foam to clean, damp hair; manually setting the hair in sections; drying the hair; and finally brushing the hair to the desired configuration. As the hair is set, each section thereof is retained in a predetermined style or configuration by the stable foam; the foam adds volume and height to the hair, as desired by the operator and customer. When the hair is placed under a dryer, the set hardens to its final state in only a few minutes. The final brushing restores any height, volume or shape lost during the drying process, in addition to removing any foam residue remaining in the hair. These and other related steps will be described in greater detail below in order to provide a full appreciation of the convenience and usefulness of the invention at hand.

Initially, it is preferable that the hair be thoroughly cleansed by washing, shampooing and rinsing. The hair is then towel dried. If desired, a rinse or conditioning agent may be applied to the hair during or after cleansing.

After the above procedures have been completed, the foam is applied to the hair. It is preferred that the foam be kept under pressure in a container such as a conventional push-button spray can. Thus, the foam can be maintained close at hand, and is readily available merely by actuating the spray can. Some of the foam is sprayed from the spray can into a dry container such as a shallow bowl. Then a portion of the foam is scooped up by the operator's fingers, with the foam being gradually applied to the customer's hair until the hair is completely permeated and covered by the foam so that the hair and foam form a pliable mass. Since the foam is stable, it will not break down into a liquid when applied to the hair.

Each section of the hair is worked by the operator's hands and fingers until the desired shape, height and volume is obtained. It is possible to exercise a variety of shaping techniques when working with a stable foam. For example, the hair can be configured into standup curls, barrel curls, simple waves, and large dip waves, as may be desired, and additionally, the hair may be divided into top, side and back sections as may be required for better manipulation and configuring.

The hair is shaped into individual curls by first raising a section of the pliable hair and foam away from the scalp, then combing same smoothly through while pulling the section of hair and foam mass in the desired direction of curl. Next, additional foam may be placed on the underside of the portion of hair to be curled (that is, on the portion of hair which will form the inside of the curl-to-be) in order to further support the base of the respective section of hair. Then, the end portion of the section of hair to be curled is turned, or curled, by the operator's fingers in the desired direction and placed adjacent the base of the formed curl near the scalp.

As stated above, the hair can also be sectioned into top, side and back portions. This is done by applying additional foam upon a respective section of hair and manually molding the hair and foam mass of the section as by using a comb. After the hair has been shaped or sculptured as desired, the hair may be lifted by a rat-tail comb or the like to give the hair height and volume, or in other words, body.

Regardless of the styling techniques used, the customer is positioned under a dryer after the hair has been shaped or sculptured as desired. In just a few minutes, the hair set will harden to its final shape, and the foam will substantially disappear, leaving at most only a light powdery residue. Even though the set has become semi-rigid, the hair should remain under the dryer until thoroughly dried (usually an additional 15 to 20 minutes).

After the hair is thoroughly dried, it is finally brushed and lifted to restore any height or volume lost due to compacting that has occurred during the wetting and drying process. During the final brushing, the hair is stroked or brushed in the same direction and in the same manner as originally shaped by hand in the presence of the foam. This eliminates the necessity of the conventional step of backcombing the hair; however, if desired, the hair may still be backcombed for additional effects.

When a customer's hair is set and styled according to the above process, the damage to hair that is caused by excessive tension and pressure that is normally incurred by the use of mechanical styling aids is eliminated. Also, a form of hair damage known as "roller splits" that often occurs when hair is wound too tightly about mechanical styling aids is precluded since such mechanical styling aids are not necessary in the practice of the present invention.

It has been observed that hair styles by the present invention tends to retain its shape at least as well as, and often better than, conventional hair styling techniques. Should a person's hair begin to lose its style between treatments, the hair can usually be recombed as required in the same manner that the hair was combed or brushed during the final brushing step of the present invention to achieve some or all of the configured forms that existed immediately following the hair styling.

In order to more fully describe the present invention, the following examples are set forth. However, it is to be understood that the examples are for illustrative purposes and are not to be construed as limiting the scope of the present invention as defined in the appended claims.

EXAMPLE

A number of hair sculpturing foam compositions were formulated and tested on human hair to determine the effectiveness of the hair sculpturing foam composition in the sculpturing of hair. One typical procedure for preparing the hair sculpturing foam compositions is hereinafter set forth. It should be noted that the particular procedure employed in formulating the hair sculpturing foam composition is not critical.

PROCEDURE

A series of substantially homogeneous aqueous compositions were prepared by admixing various constituents. The compositions were typically prepared by placing a predetermined amount of water in a container and introducing the other constituents into the water in predetermined amounts while maintaining the total system under agitation. In those instances where a combination of the water dispersible polymeric material and the surfactant were employed, the water dispersible material was first added to the water and stirred until a substantially homogeneous admixture resulted. Thereafter, the surfactant was introduced into the homogeneous admixture of the water and dispersible polymeric material and the resulting admixture agitated until a sufficiently homogeneous resulting admixture was obtained. Care was exercised to insure that the agitation was not sufficient to cause any substantial amount of foaming when the surfactant was introduced into the homogeneous mixture of the water and dispersible polymeric material. Other ingredients, which were employed in some of the compositions, were then added to the homogeneous resulting admixture containing the water dispersible polymeric material and the surfactant.

Each composition so prepared was then evaluated using the following criteria to determine if the composition was satisfactory or unsatisfactory for use as a hair sculpturing foam composition in accordance with the present invention. The criteria employed in the evaluation are as follows:

1. Residue on hair.
2. Foam stability.
3. Drying time.
4. Softness of hair.
5. Stability of wave and or curl of the sculptured hair.
6. Odor of hair both before and after drying.
7. Sheen of hair.
8. Tangling characteristics of hair sculptured using the foam composition.

In certain of the compositions a hydrolyzed polyvinyl alcohol was employed as one of the constituents. In such compositions the hydrolyzed polyvinyl alcohol was first dispersed in the water which was heated to approximately 80° C. to facilitate in the dispersing of the hydrolyzed polyvinyl alcohol. Thereafter, the surfactant and other ingredients were added to the dispersion of water and the hydrolyzed polyvinyl alcohol.

An egg beater was employed to foam four compositions numbered 1–4 of the following Table I; whereas, an aeration apparatus consisting of a bottle, an aquarium aeration, plastic tubing, and a ceramic disperser was employed to foam the other compositions:

TABLE I

AQUEOUS COMPOSITIONS AND EVALUATION OF SAME AS HAIR SCULPTURING FOAM COMPOSITIONS

| Composition No. | Water % | Surfactant Identity | % | Water Dispersible Polymeric Material Identity | % | Other Constituents Identity | % | Summary of Results of Evaluation |
|---|---|---|---|---|---|---|---|---|
| 1 | 68 | Aqueous solution containing minor amounts of a linear alkyl-benzene sulfonate and ethoxylated alkyl alcohol[a] | 10 | | | Pyridine | 1 | Unsatisfactory; foam not stable. |
| | | | | | | Sodium silicate (50% aqueous solution) | .05 | |
| | | | | | | Isopropyl alcohol | 20 | |
| 2 | 72.5 | | | gelatin[b] | 1 | Pyridine | .3 | Unsatisfactory; foam not stable. |
| | | | | | | Sodium silicate (50% aqueous solution) | 1 | |
| | | | | | | Isopropyl alcohol | 20 | |
| | | | | | | Hair Conditioner[c] | 5 | |
| 3 | 92.5 | Aqueous solution containing minor amounts of a linear alkyl-benzene sulfonate and ethoxylated alkyl alcohol[a] | 5 | gelatin[b] | 1 | Pyridine | 0.5 | Unsatisfactory; drying rate not acceptable slight residue. |
| | | | | | | Sodium silicate (50% aqueous solution) | 1 | |
| 4 | 88 | | | gelatin[b] | 1 | Sodium silicate 50% aqueous solution | 1 | Unsatisfactory; foam not stable. |
| | | | | | | Hair conditioner[c] | 10 | |
| 5 | 81 | Aqueous solution containing minor amounts of a linear alkyl-benzene sulfonate and ethoxylated alkyl alcohol[a] | | gelatin[b] | 3 | Isopropyl alcohol | 10 | Unsatisfactory; foam not stable. |
| | | | | | | Hair conditioner[c] | 3 | |
| 6 | 98 | Sodium lauryl sulfate | 1 | gelatin[b] | 1 | | | Satisfactory. |
| 7 | 97 | Sodium lauryl sulfate | 1 | gelatin[b] | 2 | | | Unsatisfactory; Styled hair too hard. |
| 8 | 96 | Sodium lauryl sulfate | 1 | gelatin[b] | 3 | | | Unsatisfactory; Styled hair too hard. |
| 9 | 94 | Sodium lauryl sulfate + Aqueous solution containing minor amounts of a linear alkyl-benzene sulfonate and ethoxylated alkyl alcohol[a] | 1  5 | | | | | Marginal foam and wave stability. |
| 10 | 97 | Sodium lauryl sulfate | 1 | | | NH$_4$OH (35% Aqueous solution) | 2 | Marginal foam stability and rate of drying. |

TABLE I-continued
AQUEOUS COMPOSITIONS AND EVALUATION OF SAME AS HAIR SCULPTURING FOAM COMPOSITIONS

| Composition No. | Water % | Surfactant Identity | % | Water Dispersible Polymeric Material Identity | % | Other Constituents Identity | % | Summary of Results of Evaluation |
|---|---|---|---|---|---|---|---|---|
| 11 | 96.5 | Sodium lauryl sulfate | 1 | gelatin[b] | | NH₄OH (35% aqueous solution) | 2 | Marginal foam stability, rate of drying and poor wave and curl stability. |
| 12 | 96 | Sodium lauryl sulfate | 1 | gelatin[b] | 0.5 | NH₄OH (35% aqueous solution) | 2.5 | Marginal foam stability and rate of drying. |
| 13 | 96 | Sodium lauryl sulfate | 1 | gelatin[b] | 0.5 | NH₄OH (35% aqueous solution) pyridine | 2.0 0.5 | Marginal foam stability and rate of drying. |
| 14 | 97.5 | Sodium lauryl sulfate | 1 | gelatin[b] | 1 | pyridine | 0.5 | Unsatisfactory; curl and wave stability. |
| 15 | 93 | Sodium lauryl sulfate | 2 | gelatin[b] | 2 | NH₄OH (35% aqueous solution Sodium silicate (50% aqueous solution) | 2 1 | Unsatisfactory; hair too hard; residue. |
| 16 | 98 | Sodium lauryl sulfate | 1 | | | Hydrolyzed gelatin[d] | 1 | Unsatisfactory; slow drying and not firm enough. |
| 17 | 98.5 | Sodium lauryl sulfate | 0.4 | | | NH₄OH (35% aqueous solution) to adjust H to 8. Hydrolyzed gelatin[d] | 0.1 1 | Unsatisfactory; not stiff enough. |
| 18 | 98.5 | Sodium lauryl sulfate | 0.5 | | | Hydrolyzed gelatin[d] | 1 | Unsatisfactory; not stiff enough. |
| 19 | 97.5 | Sodium lauryl sulfate | 0.5 | | | Hydrolyzed gelatin[d] | 2 | Unsatisfactory; not stiff enough. |
| 20 | 97 | Sodium lauryl sulfate | 1.0 | gelatin[b] | 1 | Hydrolyzed gelatin[d] | 1 | Satisfactory. |
| 21 | 96 | Sodium lauryl sulfate | 1.0 | gelatin[b] | 1 | NH₄OH (35% aqueous solution) Hydrolyzed gelatin[d] | 1 1 | Satisfactory. |
| 22 | 68 | Aqueous solution containing minor amounts of a linear alkylbenzene sulfonate and ethoxylated alkyl alcohol[a] | 10 | | | triethanol amine sodium silicate (50% aqueous solution) isopropyl alcohol | 1 0.5 20 | Unsatisfactory; would not retain curl. |
| 23 | 72.5 | | | gelatin[b] | 1 | triethanol amine sodium silicate (50% aqueous solution) isopropyl alcohol hair conditioner[c] | 0.3 1 20 5 | Unsatisfactory; foam unstable. |
| 24 | 92.5 | Aqueous solution containing minor amounts of a linear alkylbenzene sulfonate and ethoxylated alkyl alcohol[a] | 5 | gelatin[b] | 1 | triethanol amine; sodium silicate (50% aqueous solution) | 0.5 1 | Unsatisfactory; hair too hard. |
| 25 | 68 | | | gelatin[b] | 1 | sodium silicate (50% aqueous solution) hair conditioner[c] | 1 10 | Unsatisfactory; foam unstable. |
| 26 | 96 | Sodium lauryl sulfate | 1 | gelatin[b] | 3 | | | Unsatisfactory; hair too hard. |
| 27 | 95 | Sodium lauryl sulfate | 1 | gelatin[b] | 3 | Sodium silicate (50% aqueous solution) | 1 | Unsatisfactory; hair too hard; slight residue. |
| 28 | 84 | Sodium lauryl sulfate | 2 | gelatin[b] | 3 | Sodium silicate (50% aqueous solution) isopropyl alcohol | 1 10 | Unsatisfactory; hair too hard. |
| 29 | 97.5 | Sodium lauryl sulfate | 1 | gelatin[b] | 1 | Hydrolyzed polyvinyl alcohol[e] | 0.5 | Satisfactory. |
| 30 | 97 | Sodium lauryl sulfate | 1 | gelatin[b] | 1 | Hydrolyzed polyvinyl alcohol[e] | 1 | Unsatisfactory; too hard. |
| 31 | 96.5 | Sodium lauryl sulfate | 1 | gelatin[b] | 1 | Hydrolyzed polyvinyl alcohol[e] | 1.5 | Unsatisfactory; too hard. |
| 32 | 97.8 | Sodium lauryl sulfate | 1 | gelatin[b] | 1 | Hydrolyzed polyvinyl | .2 | Satisfactory. |

TABLE I-continued
AQUEOUS COMPOSITIONS AND EVALUATION OF SAME AS HAIR SCULPTURING FOAM COMPOSITIONS

| Composition No. | Water % | Surfactant Identity | % | Water Dispersible Polymeric Material Identity | % | Other Constituants Identity | % | Summary of Results of Evaluation |
|---|---|---|---|---|---|---|---|---|
| | | | | | | alcohol[e] | | |

[a] Parsons' ® Sudsy Detergent Ammonia, manufactured for Armour-Dial, Inc., Phoenix, Arizona, 85077. An aqueous solution containing ammonium hydroxide, linear alkylbenzene sulfonate, ethoxylated alkyl alcohol, opacifier clarifying agents and salts (inert).
[b] gelatin, packaged by Knox Gelatin, Inc., Englewood Cliff, New Jersey 07632.
[c] hair conditioner - "Suave" ® Balsam Protein Instant Hair Conditioner, marketed by Helene Curtis, Ind., Inc., Chicago, Illinois 60639.
[d] hydrolyzed gelatin - gelatin, packaged by Knox Gelatin, Inc., was hydrolyzed by the following procedure: 15% gelatin was added to 85% water and the pH of the resulting admixture was lowered to 2 by the addition of HCl. The resulting admixture was then heated by controlled heat to 90° C. for a period of 24 hours. During the 24 hour period the admixture was intermittently stirred. The reaction admixture was then cooled, neutralized to a pH of 7.5, and analyzed using infrared spectroscopy to determine the percent of glycine and the degree of degradation of the polymer material. The analysis is as follows: alanine, 8.7%; arginine, 9.0%; aspartic acid, 3.4%; cystine, 0.1%; glutanic acid, 5.8%; glycine, 25.5%; histidine, 0.9%; hydroxyproline, 14.4%; leucine, 7.1%; lysine, 5.9%; phenyl alamine, 1.4%; proline, 9.5% and fibrin, 8%.
[e] hydrolyzed polyvinyl alcohol, marketed by Matheson, Coleman and Bell of Cincinatti, Ohio. Ten percent of the hydrolyzed polyvinyl alcohol was added to water and dispersed therein with a mixer. Thereafter the volume of water was adjusted to a known volume. Aliquots were then used to provide the composition with the desired amount of the hydrolyzed polyvinyl alcohol.

The above data indicates that the combination of water, an effective minor amount of the water dispersible polymeric material, and an effective minor amount of a surfactant provides foam compositions which can be employed in the sculpturing of hair. However, most compositions which did not contain the water dispersible polymeric material in combination with the surfactant in minor effective amounts were either marginal or completely unacceptable for use as a hair sculpturing foam composition. Further, those compositions containing sodium silicate were, in all cases, unacceptable.

EXAMPLE 2

Equal portion of compositions number 6 and number 9 of Table I were mixed together to form a modified composition. The modified composition contained 0.5 weight percent gelatin; 1.0 weight percent lauryl sulfate; 2.5 weight percent of the aqueous admixture containing effective minor amounts of an alkylbenzene sulfate and an ethoxylated alkyl alcohol. The modified composition, when applied to human hair, was satisfactory for use as a hair sculpturing foam composition.

EXAMPLE 3

A commercially available exothermic foam waving system for use in a permanent wave, marketed under the trademark ZOTOS ® texture foam by Zotos International, Inc. of Darien, Conn. 06820, was investigated to determine if the components, other than the permanent solution, could be employed to produce a stable foam for the sculpturing of hair without the use of hair rollers, a step utilized in application of the before mentioned permanent wave system. The styling lotion was placed in a foam applicator provided with the permanent wave kit. The styling lotion would not provide a stable foam when employed without the permanent solution, whether in a cooled or warmed condition.

It is clear that the present invention is well adapted to carry out the objects and obtain the ends and advantages mentioned herein as well as those inherent in the invention. While a presently preferred embodiment of the invention has been described for purposes of this disclosure, numerous changes may be made which will readily suggest themselves to those skilled in the art and which are accomplished within the spirit of the invention disclosed and as defined in the appended claims.

What is claimed is:

1. An improved method for styling hair, comprising the steps of:
    applying a stable foam, capable of retaining its form upon manipulation, to clean, damp hair to form a pliable mass of hair and foam;
    shaping the pliable mass in sections, each section being retained, unassisted by mechanical styling aids, in a determined sculptured shape by the stable foam;
    drying the shaped pliable mass, the pliable mass becoming set in a semi-rigid sculptured shape upon drying the foam; and
    brushing the semi-rigid hair to finally shape the hair and to remove the foam residue.

2. The method of claim 1 further comprising the following steps prior to applying the stable foam: shampooing the hair; and rinsing the hair.

3. The method of claim 2 wherein the brushing step is characterized as first back-combing the hair.

4. In the application of a styled hairdo to a person's hair which includes wetting the person's hair, setting the person's hair, drying the set hair, and combing the hair, the improvement comprising:
    stable foam means serving as a training aid for retaining the hair in a determined sculptured shape during the setting of the hair, said foam means maintaining its foam characteristics during the manipulation of the person's hair during the setting of same, said foam means being the same for setting the hair and unassisted by mechanical styling aids.

5. An improved method for styling a person's hair, comprising the steps of:
    a. wetting the hair;
    b. sectioning the hair into a plurality of hair sections;
    c. applying a stable form, capable of retaining its form upon manipulation, to a first hair section to form with the hair thereof a pliable mass;
    d. shaping the pliable mass of the first hair section into a determined sculptured configuration, the pliable mass being retained in said configuration by the stable form, unassisted by mechanical styling aids;
    e. applying the stable foam to other hair sections and repeating in order steps (c) and (d) above until all of the hair sections have been shaped into determined sculptured configurations;
    f. drying the hair until the foam has disappeared except for forming a residue; and
    g. combing the dried hair to finally shape the hair and to substantially remove the foam residue.

* * * * *

UNITED STATES PATENT AND TRADEMARK OFFICE
CERTIFICATE OF CORRECTION

PATENT NO. : 4,299,240
DATED : November 10, 1981
INVENTOR(S) : Coleda J. Failing It is certified that error appears in the above-identified patent and that said Letters Patent are hereby corrected as shown below:

On the title page, the address of the Inventor should be Enid, Oklahoma, instead of Oklahoma City, Oklahoma. The address for the Inventor is:

> Coleda J. Failing
> 2109 W. Broadway
> Enid, Oklahoma 73701

Signed and Sealed this

Eleventh Day of May 1982

[SEAL]

*Attest:*

GERALD J. MOSSINGHOFF

*Attesting Officer*  *Commissioner of Patents and Trademarks*